United States Patent
Oka et al.

(10) Patent No.: US 6,201,023 B1
(45) Date of Patent: Mar. 13, 2001

(54) METHODS AND COMPOSITIONS TO PROTECT CROPS AGAINST PLANT PARASITIC NEMATODES

(75) Inventors: Yuji Oka, Rehovot; Yitzhak Spiegel, Rishon Lezion; Yigal Cohen, Kiryat Ono, all of (IL)

(73) Assignee: Agrogene Ltd., Kiryat Ono (IL)

( * ) Notice: Subject to any disclaimer, the term of this patent is extended or adjusted under 35 U.S.C. 154(b) by 0 days.

(21) Appl. No.: 08/872,186

(22) Filed: Jun. 10, 1997

(51) Int. Cl.$^7$ .................................................. A01N 37/12
(52) U.S. Cl. .......................... 514/561; 514/513; 514/538; 514/551; 514/567; 514/626; 560/38; 560/41; 560/155; 562/26; 562/443; 562/450; 564/197; 564/198
(58) Field of Search .................... 562/553, 26, 443, 562/450; 514/551, 561, 567, 626, 538, 513; 560/155, 38, 41; 564/197, 198

(56) References Cited

FOREIGN PATENT DOCUMENTS

| | | |
|---|---|---|
| 0 268 775 | 9/1987 | (EP). |
| 0 288 976 | 4/1988 | (EP). |
| 0 313 512 | 8/1988 | (EP). |

OTHER PUBLICATIONS

Ryals, et al., "Systemic Acquired Resistance", *The Plant Cell*, vol. 8, pp. 1809–1819 (1996).

Trudgill, D.L., "Resistance to and Tolerance of Plant Parasitic Nematodes in Plants", *Annu. Rev. Phytopathol.*, 29:167–192 (1991).

Kaloshian, et al., "Resistance Breaking Nematodes Identified in California Tomatoes", *California Agriculture*, vol. 50, No. 6, pp. 18–19, (1996).

Ogallo et al., "Systemic Acquired Resistance and Susceptibility to Root–Knot Nematodes in Tomato", *Phtopathology*, vol. 86, No. 5, pp. 498–501 (1996).

Williamson et al, "Nematode Pathogenesis and Resistance in Plants", *The Plant Cell*, vol. 8, pp. 1735–1745, (1996).

Davies et al, "Asymetric Synthesis of R–β–Amino Butanoic Acid and S–β–Tyrosine: Homochiral Lithium Amide Equivalents for Michael Additions to α, β–Unsaturated Esters", *Tetrahedron Asymetry*, vol. 2, No. 3, pp. 183–186, (1991).

Zilkha et al., "Sysnthesis of DL–β–Aminobutyric Acid and Its N–Alkyl Derivitives", JoC, 23:94–96 (1957).

Cohen, Y., "3–Aminobutyric Acid Induces Systemic Resistance Against *Peromospore Tabacina*" *Physiological and Molecular Plant Pathology*, 44:273–288 (1994).

Cohen et at., "Systemic Translocation of $^{14}$ C–DL–3 Aminobutyric Acid in Tomato Plants in Relation to Induced Resistance Against *Phytophthora Infestans*", *Physiological and Molecular Plant Pathology*, 45:441–446, (1994).

Cohen et al., "β–Aminobutyric Acid Induces the Accumulation of Pathenogenesis–Related Protoens in Tomato (*Lycopersicon esculentum L.*) Plants and Resistance to Late Blight Infection Caused by *Phytophthora Infestans*", *Plant Phsiol.*, 104:59–66, (1994).

Cohen, Y., "Local and Systemic Control of *Phytophthora Infestans* in Tomato Plants by DL–3–Amino–n–Butanoic Acids", *Phytopathology*, 84(1): 55–59 (1993).

*Primary Examiner*—Michael L. Shippen
(74) *Attorney, Agent, or Firm*—Mark M. Friedman

(57) ABSTRACT

A method for protecting a crop against plant-parasitic nematode attack by inducing local and systemic resistance of the crop comprising the application of a composition containing an effective amount of β-amino butyric acid or derivatives thereof to the crop or its locus.

6 Claims, No Drawings

METHODS AND COMPOSITIONS TO PROTECT CROPS AGAINST PLANT PARASITIC NEMATODES

FIELD AND BACKGROUND

The present invention concerns compounds, compositions and methods for protecting crops from nematode attack. More specifically, the present invention is directed to compounds and compositions, which, when used as a dressing for seeds or tubers of a crop, or when applied directly to the crop or its locus, induce local and systemic resistance of the crop against attacks caused by soil-borne plant-parasitic nematodes. Such action is hereinafter defined as "systemic acquired resistance (SAR)".

Nematodes are a large group of parasites which attack both plants and animals. Plant-parasitic nematodes are obligate parasites, obtaining nutrition only from the cytoplasm of living plant cells. These nematodes are tiny round worms, about one mm long, that damage food and fiber crops throughout the world and cause billions of dollars in losses annually (Williamson and Hussey, The Plant cell 8: 1735–1745, 1996). Hereinafter, unless otherwise stated, the term "nematodes" will refer to soil-borne plant-parasitic nematodes.

Over 20% of the annual yield losses of major crops in the world occur from plant-parasitic nematodes: monetary losses due to nematodes is estimated to be US $100 billion worldwide. There is a correspondingly large market for nemacides, or agents which kill nematodes and suppress nematode infections.

Most of the economic damage is caused by the sedentary endoparasitic nematodes of the family Heteroderidae. This family is divided into the cyst nematodes (Heterodera and Globodera) and the root-knot nematodes (Meloidogyne). The root-knot nematodes, so-called for the root galls (root knots) that they form on many hosts, infect thousands of plant species and cause severe losses in yield of many crops (vegetables and fruits) as well as flowers and other ornamentals. Symptoms of diseased plants include stunting, wilting and susceptibility to other diseases. During the infection process, elaborate developmental and morphological changes occur in host root cells especially in those become the feeding cells that provide the sole source of nutrients for the nematode. The life cycle of the root-knot nematode has a series of four stages. In the infective stage the nematodes are mobile, second-stage juveniles (J2) which emerge from the egg and find a host. After finding a host, each of the J2 nematodes penetrates the root. Then, the J2 nematode migrates to the root tip and finally proceeds to the differentiation zone where procambial host cells adjacent to the head of the nematode develop into "giant cells". These large multinucleate metabolically active cells serve as a permanent source of nutrients for the endoparasite (Williamson and Hussey, The Plant Cell 8: 1735–1745, 1996). Concurrent swelling and division of cortical cells around the nematode lead to the formation of galls typical of Meloidogyne spp.

After feeding is initiated, the nematode becomes a sedentary adult female following three molts which occur approximately 11 through 16 days after the initiation of feeding. After the last molt, the adult female continues to grow until it becomes a non-motile, saccate, egg-laying female. Egg production begins 3–5 weeks after the infection starts; eggs are released and the infection cycle may start again. Males regain motility during the third molt before leaving the root.

Chemical treatment of the soil is one of the most promising means to control plant-parasitic nematodes. This control method depends upon bringing the nematode-toxic chemicals into contact with the nematode in sufficiently high concentrations. Such contact may be accomplished by percolation of the chemicals in water or a gaseous diffusion of a nematocide in the soil. The nematocide must penetrate the nematode body in order to kill it, either through the cuticle or body openings, or during feeding.

Methyl bromide, organophosphates and carbamates are widely used nematocides, which unfortunately are highly hazardous to the enviroment. Organophosphates and carbamates paralyze the nematode by inhibiting acetylcholinesterase enzyme activity which is essential for neural activity (The Pesticide Manual, 10th Edition, 1994, Crop Protection Publications, 1341 pp.).

Another way to control nematodes is by using genetically-resistant cultivars. Plants are defined as resistant to nematodes when they are able to reduce the level of nematode reproduction (Trudgill, Ann. Rev. Phytopathol 29: 167–193, 1991). Nematode resistance genes are present in several crop species such as tomato, potato, soybean and cereals. With many of these resistance genes, a localized necrosis or hypersensitive response, resembling that described for other pathogens resistance genes, is associated with nematode infection. One such resistance gene is the Mi in tomato which confers resistance against root-knot nematodes (Williamson and Hussey, The Plant Cell 8: 1735–1745, 1996). However, this resistance gene was recently reported to be unstable (Kaloshian et al., Cal. Agri., 50:18–19, 1996).

A third strategy is to induce plant resistance against pest organisms by adding various chemicals to the plants themselves. While the strategy of inducing systemic acquired resistance (SAR) has been extensively used by commercial companies to protect plants from fungal attack, no such strategy has been used against nematode attack. Systemic acquired resistance (SAR) in plants is gained by either a primary inoculation with an incompatible pathogen (virus, bacterium, fungus) that induces a hypersensitive local lesions in the host, from which a signal is translocated to untreated parts of the plant so as to protect them from diseases caused by fungi, bacteria or viruses, or by using a chemical which has no direct effect on plant pathogenic organisms, but rather can induce a SAR response (Ryals et al—Plant Cell, 8: 1809–1819; 1996).

SAR in a crop is manifested by various defence mechanisms including the accumulation in the crop of soluble proteins referred to as pathogenesis-related (PR) proteins. Some PR-proteins have been shown to be hydrolytic enzymes such as chitinases and β-1,3 glucanases, while others are shown to be peroxidases. Also accumulated is a group of proteins having a molecular weight of about 10 to 20 kDaltons which are called P14 proteins, which are also known to possess antifungal function. All of these proteins are believed to participate in the defense system of a crop.

Various isonicotinoyl-pyridinyl-hydrazin-derivatives and benzothiadiazole compounds have been described in patent literature as immunizing healthy plants against fungal diseases (European Patent Applications 0 268 775, 0 288 976 and 0 313 512).

Another class of molecules is DL-3-aminobutyric acid (BABA) and derivatives which have been shown to induce local and systemic resistance against fungal attack (Cohen et al., Plant Physiology 104: 59–66, 1994; Cohen, Phytopathology 84: 55–59, 1994; Cohen, Physiol. Molecular Plant Pathol. 44: 273–288). The use of BABA against fungal attack in crop plants has been described in several patent applications: Israel Application No. IL107,992; Israel Application No. IL109,474; Israel Application NO. IL111,828; PCT Application No. US 94/14,108; PCT Application No. WO95/15, 684. However, these compounds have never been examined for their efficacy against species of plant-parasitic nematodes.

Little information is available on the induction of plant resistance against nematodes. Ogalo and McClure (*Phytopatholgy* 86: 498–501, 1996) reported that a prior inoculation of tomato roots with the incompatible nematode *Meloidogyne incognita* induced resistance against the compatible nematode *M. hapla*. However, no direct induction with a chemical composition has been demonstrated.

It would therefore be highly useful to have a chemical composition which can induce plant resistance to nematodes when applied directly to the whole plants or a portion thereof

SUMMARY OF THE INVENTION

According to the present invention, there is provided a method for treating a crop against a disease caused by a nematode species, including the step of applying a compound to a portion of the crop, said compound having a formula (I):

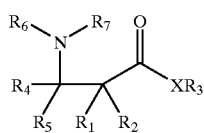

(I)

wherein
$R_1$ and $R_2$ are independently hydrogen, $C_{1-8}$alkyl, phenyl, and phenyl-$C_{1-4}$alkyl;
$R_3$ is hydrogen; $C_{1-23}$alkyl; carboxy-$C_{1-4}$alkyl; phenyl-$C_{1-4}$alkyl wherein the phenyl moiety is unsubstituted or monosubstituted by halogen; or
$C_{2-23}$alkoxycarbonyl-$C_{1-4}$alkyl;
$R_4$ and $R_5$ are independently hydrogen or $C_{1-8}$alkyl;
$R_6$ and $R_7$ are independently hydrogen, $C_{1-8}$alkanoyl; phenyl-$C_{1-4}$alkyl wherein the phenyl moiety is unsubstituted or monosubstituted by halogen;
$C_{2-8}$-alkoxycarbonyl; $CONHR_8$ wherein $R_8$ is hydrogen, $C_{1-8}$alkyl, phenyl, phenyl-$C_{1-4}$alkyl; phenyl-$C_{2-4}$ alkyloxycarbonyl, and
X is O, S or N;
and salts thereof Preferably, the compound is applied in an amount sufficient to induce resistance of the crop to the nematode species. Preferably, $R_1$ and $R_2$ are independently hydrogen, methyl or phenyl, $R_3$ is hydrogen, $R_4$ and $R_5$ are independently hydrogen or $C_{1-3}$alkyl, $R_6$ and $R_7$ are independently hydrogen, $C_{1-6}$alkyl or benzyl optionally substituted by halogen and X is oxygen. Most preferably, $R_1$ is hydrogen or methyl, $R_2$ is hydrogen, $R_4$ is hydrogen or methyl, $R_5$ is hydrogen, $R_6$ is hydrogen or methyl and $R_7$ is hydrogen. Preferably, the compound of formula I is R-β-aminobutyric acid or β-aminovaleric acid.

According to another embodiment of the present invention, the compounds of formula I protect crop plants against nematodes when combined with KOH-neutralized solution of $H_3PO_3$.

According to yet another embodiment of the present invention, there is provided a compound having a formula (I);

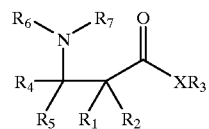

(I)

wherein
$R_1$ and $R_2$ are independently hydrogen, $C_{1-8}$alkyl, phenyl, and phenyl-$C_{1-4}$alkyl;
$R_3$ is hydrogen; $C_{1-23}$alkyl; carboxy-$C_{1-4}$alkyl; phenyl-$C_{1-4}$alkyl wherein the phenyl moiety is unsubstituted or monosubstituted by halogen; or
$C_{2-23}$alkoxycarbonyl-$C_{1-4}$alkyl,
$R_4$ and $R_5$ are independently hydrogen or $C_{1-8}$alkyl;
$R_6$ and $R_7$ are independently hydrogen, $C_{1-8}$alkanoyl; phenyl-$C_{1-4}$alkyl wherein the phenyl moiety is unsubstituted or monosubstituted by halogen;
$C_{2-8}$alkoxycarbonyl; $CONHR_8$ wherein $R_8$ is hydrogen, $C_{1-8}$alkyl, phenyl, phenyl-$C_{1-4}$alkyl; phenyl-$C_{2-4}$ alkyloxycarbonyl; and
X is O, S or N;
and salts thereof, with the proviso that the compound is not R-β-aminobutyric acid or β-aminovaleric acid.

DESCRIPTION OF THE INVENTION

Unexpectedly, it has now been found that compounds of the formula (I) hereinafter defined are effective as SAR agents against nematode diseases caused by soil-borne plant-parasitic nematodes.

The present invention particularly concerns compounds of the formula (I)

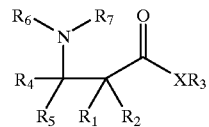

(I)

wherein
$R_1$ and $R_2$ are independently hydrogen, $C_{1-8}$alkyl, phenyl, and phenyl-$C_{1-4}$alkyl;
$R_3$ is hydrogen; $C_{-1-23}$alkyl; carboxy-$C_{1-4}$alkyl; phenyl-$C_{1-4}$alkyl wherein the phenyl moiety is unsubstituted or monosubstituted by halogen, or
$C_{2-23}$alkoxycarbonyl-$C_{1-4}$alkyl;
$R_4$ and $R_5$ are independently hydrogen or $C_{1-8}$alkyl;
$R_6$ and $R_7$ are independently hydrogen; $C_{1-8}$alkanoyl; phenyl-$C_{1-4}$alkyl wherein the phenyl moiety is unsubstituted or monosubstituted by halogen;
$C_{2-8}$alkoxycarbonyl; $CONHR_8$ wherein $R_8$ is hydrogen, $C_{1-8}$alkyl, phenyl, phenyl-$C_{1-4}$alkyl; phenyl-$C_{2-4}$ alkyloxycarbonyl; and
X is O, S or N;
and salts thereof.

Hereinafter, the term "alkyl" refers to straight carbon chains, and branched and cyclic carbon chains, which preferably contain one to four carbon atoms. For example, the term "$C_{1-8}$alkyl" refers to a straight, branched or cyclic carbon chain with from about 1 to about 8 carbon atoms. The term "phenyl-$C_{1-8}$alkyl" refers to a phenyl moiety substituted with a straight, branched or cyclic carbon chain with from about 1 to about 8 carbon atoms.

According to preferred embodiments of the present invention, $R_1$ and $R_2$ are preferably independently hydrogen, methyl or phenyl, more preferably $R_1$ is hydrogen or methyl and $R_2$ is hydrogen. $R_3$ is preferably hydrogen. $R_4$ and $R_5$ are preferably independently hydrogen or $C_{1-3}$alkyl, more preferably $R_4$ is hydrogen or methyl and $R_5$ is hydrogen. $R_6$ and $R_7$ are preferably independently hydrogen, $C_{1-6}$alkyl, or benzyl which is optionally substituted by halogen. More preferably $R_6$ is hydrogen or methyl and $R_7$ is hydrogen. X is preferably oxygen.

Particularly preferred compounds of the invention are R-β-aminobutyric acid and β-aminovaleric acid. Preferred salt forms of the compound of formula I contemplated in this application include acid addition salts such as those obtained by the additon of HCl, $CF_3CO_2H$, toluene sulfonic acid, methane sulfonic acid and $(CO_2H)_2$, as shown in Formula II:

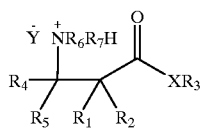

wherein Y is the residue of the acid; alkali metal salts such as those obtained by treatment with NaOH, KOH or LiOH, as shown in Formula III:

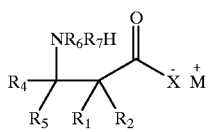

wherein M is an alkali metal such as Na, K or Li; and acid addition/amine salts such as those obtained by treatment with HCl and an amine such as diethylamine, propyl amine, benzylamine, as shown in Formula IV:

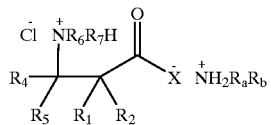

wherein $R_a$ and $R_b$ are substituents of the amine.

Hereinafter, the following abbreviations will be used: DL-β-aminobutyric acid (BABA), DL-α-aminobutyric acid (AABA); γ-aminobutyric acid (GABA); DL-β-aminoisobutyric acid (iso-BABA); DL-α-aminoisobutyric acid (isoAABA); and the R and S enantiomers of BABA (R-BABA and S-BABA).

Hereinafter, the term "nematode species" refers to a species of plant-parasitic nematodes. Examples of nematode species include, but are not limited to, sedentary endoparasitic nematodes of the family Heteroderidae, such as cyst nematodes (Heterodera) and root-knot nematodes (Meloidogyne). Hereinafter, the term "J2" refers to the nematode in the infective stage of the nematode life cycle, in which the nematode is a mobile, second-stage juvenile which emerges from the egg to find a host.

Hereinafter, the term "crop" includes any plant species to which the compounds and/or compositions of the present invention can be administered. Examples of crops include, but are not limited to, tomato, wheat and barley plants. Hereinafter, the term "administered" refers to any method of application of the compounds and/or compositions of the present invention including, but not limited to, spraying onto the adaxial leaf surfaces of the plant and drenching by direct application to the soil. Hereinafter, the term "a portion of a crop" includes tubers, seeds, leaves or any portion of the foliage of the plant, roots or the locus of the crop. Hereinafter, the term "resistance" refers to the ability of the plant roots to resist infection by, and suppress reproduction of, the nematode species.

Hereinafter, the terms "systemic acquired resistance" and SAR refer to overall, systemic resistance to a particular pathogen which is gained by induction of hypersensitive local lesions in a plant, either by primary inoculation with an incompatible pathogen (virus, bacterium, fungus), or by using a chemical which has no direct effect on plant pathogenic organisms, but which can induce a SAR response. Hereinafter, the term "treating" refers to both administering the compounds and/or compositions of the present invention substantially before an infection with a nematode species has occurred, as well as to administering the compounds and/or compositions of the present invention substantially after an infection with a nematode species has occurred.

DESCRIPTION OF PREFERRED EMBODIMENTS

The present invention is of compositions and methods to protect plants against nematode infections.

The invention is illustrated by the following examples, which describe the synthesis of various compounds of the present invention, preparation of compositions including these compounds, and methods of using these compositions against nematode infections in plants. It should be noted that these examples are intended as illustrations only and are not meant to be limiting.

Synthesis of Compounds of the Present Invention

The novel compounds encompassed by this application are structurally related to known compounds and can be easily prepared by either derivatizing the known compounds or by modifying the procedures for preparing the known compounds, as required. These procedures will be apparent to those skilled in the art. The following procedures are illustrative.

Preferred compounds of Formula V according to the present invention can be synthesized as follows. These compounds have the following structure:

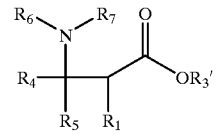

wherein $R_1$ and R4-7 are as previously defined and $R_3'$ represents hydrogen or $C_{1-8}$alkyl. These compounds can be obtained by using a compound of the formula VI as a precursor:

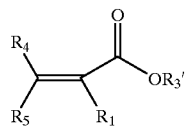

Compounds of the formula VI are either known or obtainable from known compounds according to standard procedures which are well known in the art and which would be obvious to one of ordinary skill in the art.

For example, to prepare compounds of formula V where $R_6$ is H and $R_7$ is as previously defined, the compound of formula VI is reacted with $NR_7H2$, wherein $R_7$ is as previously defined. Reactions of this type are well known in the art and have been extensively described in the literature, e.g., by A. Zilkha and J. Rivlin, *JoC* 1957, 23:94, herein incorporated by reference as an example of a method of performing such a reaction.

As another example, to prepare compounds of formula V where $R_6$ and $R_7$ are as previously defined but are not hydrogen, the compound of formula VI is reacted with $NR_6R_7Li$, wherein $R_6$ and $R_7$ are as previously defined but are not hydrogen. Reactions of this type are well known in the prior art and have been described in the literature, e.g., by Davies et al., *Tetrahedron Asymmetry*, Vol. 2, No. 3, pp. 83–186 (1991), herein incorporated by reference as an example of a method of performing such a reaction.

As can be appreciated, in such cases where $R_4$ and $R_5$ are not identical, the carbon atom to which they attach is chiral. Procedures for preparing each enantiomer form are either specifically described in the literature, e.g. in European Application No. EP 0 144 980, herein incorporated by reference as an example of such a procedure, or in Davies et al., *Tetrahedron: Asymmetry*, Vol. 2, No 3, pp. 83–186 (1991) or can be prepared according to analogous procedures which are well known in the art.

EXAMPLE 1

N-(2-Hydroxyethyl)-3-aminobutyric acid

A solution of 86 g of crotonic acid (1 mole) and ethanolamine (1 mole) in pyridine (200 ml) was refluxed for 2–3 hours and subsequently cooled. The resulting product was filtered and recyrstallized to yield the title compound having a m.p. (melting point) of 178–180° C. (compound 1.1, List of Compounds).

Following an analogous procedure, the compounds 1.2–1.7, 1.10, 1.11, and 1.13–1.15 set forth in the List of Compounds were obtained.

EXAMPLE 2

3-aminohexanoic acid

A mixture of 2-hexanoic acid (7.0 g, 0.06 mol) and concentrated aqueous aminonium hydroxide (70 ml) was heated for 24 hours in an autoclave at 150° C. The cooled mixture was treated with carbon black and filtered. After evaporation of the solvent the crude product was re-crystallized from ethanol to give the title compound with a m.p. of 203° C. (compound 1.21, List of Compounds).

Following an analogous procedure, the compounds 1.8, 1.9, 1.12 and 1.18–1.20 of List of Compounds were obtained.

EXAMPLE 3

N-Benzoyl-3-aminobutyric acid

To a cooled solution of 3-aminobutyric acid (13 g) in 2 M NaOH (130 ml) benzoyl chloride (19.7 g) was added over the course of two hours. The mixture was allowed to warm to room temperature. Washing with diethyl ether, acidifying of the aqueous phase with 20% HCl, extraction with diethyl ether, drying over $MgSO_4$, evaporation of the solvent and re-crystallization in ether/hexane gave the title compound with a m.p. of 150–152° C. (compound 1.16, List of Compounds).

Following an analogous procedure, compound 1.17 of the List of Compounds was obtained.

List of Compounds of the Formula $$R_4 - \underset{R_5}{\overset{NHR_6}{C}} - \underset{R_1}{\overset{}{C}} - COOH$$

| Cpd | $R_1$ | $R_4$ | $R_5$ | $R_6$ | m.p.(° C.) |
|-----|-------|-------|-------|-------|------------|
| 1.1 | H | $CH_3$ | H | hydroxyethyl | 178–180 |
| 1.2 | H | $CH_3$ | H | isopropyl | 167–169 |
| 1.3 | H | $CH_3$ | H | benzyl | 178–180 |
| 1.4 | H | $CH_3$ | H | cyclohexyl | 161–163 |
| 1.5 | H | $CH_3$ | H | n-hexyl | 151–153 |
| 1.6 | H | $CH_3$ | H | p-chlorobenzyl | 152–154 |
| 1.7 | H | H | H | benzyl | 180–182 |
| 1.8 | H | ethyl | H | H | 128–130 |
| 1.9 | H | $CH_3$ | $CH_3$ | H | 216 |
| 1.10 | $CH_3$ | H | H | benzyl | 148 |
| 1.11 | H | $CH_3$ | H | phenylethyl | 164 |
| 1.12 | H | phenyl | H | H | 220–221 |
| 1.13 | H | $CH_3$ | H | n-octyl | 150 |
| 1.14 | H | $CH_3$ | H | n-decyl | 148 |
| 1.15 | H | ethyl | H | benzyl | 157–160 |
| 1.16 | H | $CH_3$ | H | benzoyl | 150–152 |
| 1.17 | H | $CH_3$ | H | benzyloxycarbonyl | 128–130 |
| 1.18 | H | ethyl | H | H | 178–180 |
| 1.19 | H | $CH_3$ | H | H | 209–210* |
| 1.20 | H | $CH_3$ | H | $CH_3$ | 86–87** |
| 1.21 | H | propyl | H | H | 203 |

*enantiomer
**monohydrate

EXAMPLE 4

N-Benzyloxycarbonyl-3-aminobutyric acid 4-chlorophenyl)-1-ethylamide

Z-protected β-aminobutyric acid (0.02 g), (4-chlorophenyl)-1-ethylamine and 1.1 equivalents of DCC (dicyclohexylcarbodiimide) were stirred in ethyl acetate at room temperature for 16 hours. The precipitate was filtered, and the filtrate was evaporated and chromatographed on silica gel (hexane/ethyl acetate 1:1) to give the title compound as a mixture of diastereomers with a m.p. of 168–178° C.

Examples of Methods of Preparation of Salts of Compounds of the Present Invention

EXAMPLE 5

β-aminobutyric acid hydrochloride 5.15 g β-aminobutyric acid (50 mmol) was dissolved in 650 ml methanol. After the addition of 5.5 ml concentrated HCl, the solution was evaporated. The residue was triturated in diethyl ether, decanted and dried. A colorless oil was isolated. Microanalysis to determine the relative proportions of each atom in the compound yielded the following results: C, 34.4; H, 7.2; N, 10.0; Cl, 25.4.

EXAMPLE 6

β-aminobutyric acid sodium salt 2.06 g β-aminobutyric acid (20 mmol) was dissolved in 100 ml of a mixture of water: metanol (1:1). One equivalent NaOH in 10 ml water was added. The solution was evaporated and the resulting amorphous solid was dried. Microanalysis of the resultant dried solid yielded the following results: C, 37.4; H, 6.7; N, 10.9.

EXAMPLE 7

β-aminobutyric acid diethylammonium chloride 1.4 g β-aminobutyric acid (10 mmol) was dissolved in 100 ml of methanol. Diethylamine (0.9 g, 12.3 mmol) was added and the residue was evaporated. The oily residue was washed with ether, decanted and dried to yield an amorphous material. 1H-NMR (CD3OD, 200 MHz) 1.29 (m, 9H, 3 CH3); 2.25–2.45 (m, 2H, CH2); 314 (q, 4H, CH2CH3); 3.34–3.58 (m, 1H, CH).

EXAMPLE 8

Effect of Compounds of the Present Invention

As previously mentioned, the compounds of formula I are effective in activating or enhancing defense system of crops against nematode infections caused by soil-borne plant-parasitic nematodes. Such activity can be demonstrated in the following tests.

The root-knot nematode $M.$ $javanica$ was propagated on tomato ($Lycopersicon$ $esculentum$ Mill cv. Hosen Eilon) in the greenhouse, or aseptically in Petri dishes containing excised root cultures of tomato. Eggs were separated from egg masses with sodium hypochlorite (0.5%, 1 minute) and hatched in twice diluted 0.1 M phosphate buffer saline, pH 7.2 (PBS/2) to obtain infective J2.

Tests were conducted with DL-β-aminobutyric acid (BABA), DL-α-aminobutyric acid (AABA); γ-aminobutyric acid (GABA); DL-β-aminoisobutyric acid (iso-BABA); DL-α-aminoisobutyric acid (isoAABA). The R and S enantiomers of BABA (R-BABA and S-BABA) were tested as well.

Chemicals were applied at concentrations in the range of 0.01 to 0.2% viz. 100 to 2000 ppm (for BABA these concentrations are equivalent to 1 to 20 mM). Water solutions were either sprayed (1 ml/plant) onto the adaxial leaf surfaces of the plant, or drenched (10 ml/plant/pot) by direct application on the soil surface, unless otherwise stated. As a control, water was sprayed or drenched.

The pot experiments were conducted in a temperature-controlled greenhouse (25±2° C.), with 14 h light photoperiod. Plants were fertilized with NPK nutrient solution (75 mg/liter) and irrigated with plain tap water as needed. Twenty to thirty days after seeding plants were inoculated with the nematodes. After a certain period of incubations (see below), plants were removed from soil and the following parameters were recorded: top fresh weight, root fresh weight, root-galling (evaluated on a 0–5 scale) and the number of nematode eggs per root.

Test 1. The specific activity of BABA against nematode attack caused by $M$ $javanica$ in tomato plants was tested. The experimental method was as follows. The experiments were conducted with 3-week-old tomato plants. One ml of 2,000 ppm aminobutyric acid solution dissolved in water was sprayed on each plant (2 mg per plant), or 10 ml of 2000 ppm solution was drenched to the soil (20 mg/pot). One day after treatment, each plant was inoculated with 1000 second-stage juveniles of $M.$ $javanica$. Data were collected 4 weeks after inoculation.

The experiment was repeated 3 times with 5 plants for each treatment. Means within a column followed by a common letter are not different, according to Tukey's HSD (P=0.05).

TABLE 1

The effect of aminobutyric acid isomers on tomato plants infected by the root-knot nematode $Meloidogyne$ $javanica$

| Treatment | Chemical | Top fresh wt (g/plant) | Root fresh wt (g/root) | Galling index (0–5 visual scale) | No. of eggs/plant (× 100) |
|---|---|---|---|---|---|
| Spray | Water | 9.2 a | 3.4 a | 3.4 a | 1,156 a |
|  | AABA | 4.4 b | 3.3 a | 1.1 b | 898 b |
|  | BABA | 8.2 a | 3.4 a | 0.8 b | 464 c |
|  | GABA | 8.8 a | 3.7 a | 3.7 a | 1,316 a |
| Soil | Water | 9.2 a | 3.4 b | 3.4 a | 1,136 b |
| drench | AABA | 10.2 a | 3.8 b | 3.2 a | 1,292 b |
|  | BABA | 8.3 a | 3.1 b | 2.5 b | 418 c |
|  | GABA | 8.9 a | 4.7 a | 3.6 a | 1,584 a |

Data in Table 1 show that BABA applied as a spray to the foliage significantly reduced the galling on the nematode-infected root system as compared to the control, non-treated infected plants. This also caused a reduction (by 60%) in the number of eggs per root thus decreasing the ability of the nematode reproduction. AABA reduced galling as well as egg production to a lesser extent than BABA, while GABA had no effect on these parameters. Spray application with AABA was toxic to the foliage whereas BABA and GABA caused no phytotoxic effects.

Data in Table 1 also show that BABA reduced, significantly, galling and egg production when applied as a soil drench, without affecting the plant growth; AABA or GABA did not cause such effect. Interestingly enough, isoAABA and isoBABA did not reduce nematode attack on the plants (data not shown).

Test 2. The direct effect of aminobutyric acids on $M.$ $javanica,$ in vitro was tested. The experimental procedure was as follows.

Sixty J2 were incubated, at 27° C., in 0.5 ml of water, AABA, BABA or GABA at concentrations ranged between 200 to 2,000 ppm. The experiments were conducted in 24-well titer plates (Nunk, Denmark). After 3 days, the number of immobilized J2 was counted. Five replicates were used for each treatment and the experiment was conducted 3 times.

The results showed that none of the chemicals caused any significant immobilization of the J2 as compared to the non-treated, water control. These results clearly indicated that BABA, which protects tomato roots against nematode attack by reducing galling and egg production, is not directly toxic to the nematode but rather operates via the plant. Data published by Cohen and Gisi (Physol. and Molecular Plant Pathol 45: 441–456, 1994) have demonstrated that $^{14}$C-BABA applied to tomato foliage moves to the root system. It has also been demonstrated that $^{14}$C-BABA which is applied to the foliage of $M.$ $javanica$-infected tomato moves to the root system and accumulates in the galls produced by the nematode adult females (data not shown).

Without wishing to be limited to a single mechanism, it would appear that BABA applied to the foliage reaches the roots via the phloem and makes the roots much less susceptible to nematode attack. A soil drench treatment with BABA (Table 1) caused protection against nematode attack due to the accumulation of BABA in the root and especially the galling system. In support of this hypothesis, Cohen and Gisi ($Physol.$ $and$ $Molecular$ $Plant$ $Pathol,$ 45: 441–456, 1994) have shown that $^{14}$C-BABA can be absorbed directly by, and accumulates in, tomato roots.

Test 3. The timing for optimal BABA treatment was examined. The experimental method was as follows.

Three-week-old tomato plants grown in 50 ml pots, were sprayed with either water or 2 mg/plant BABA solution and inoculated with 100 J2 per pot, 0, 1 or 3 days after the treatments. Four days after inoculation plants were uprooted, washed, and the roots were stained with acid fucsin. Root galling and the number of J2 which penetrated the root system were recorded. Each treatment included 8 replicates and the experiment was conducted 3 times. Results are presented in Table 2.

TABLE 2

Timing effect of nematode inoculation on BABA efficacy against the root-knot nematode *Meloidogyne javanica* in tomato

| Inoculation timing | Spray treatment | | | |
|---|---|---|---|---|
| (days after inculation | Water | | BABA (2 mg/pl) | |
| with nematodes) | G.I. | J2/root | G.I. | J2/root |
| 0 | 4.0 | 52.6 | 0.2 | 13.0 |
| 1 | 4.2 | 60.4 | 0.5 | 13.3 |
| 3 | 3.7 | 59.5 | 0.2 | 12.8 |

The G.I. or galling index was recorded on a 0–5 scale. All data in BABA-treated plants were significantly (P<0.05) different from the corresponding data in the water (control)-treated plants.

Data in Table 2 indicated that BABA significantly reduced both galling and the establishment of J2 in the tomato roots as compared to the water-treated plants which served as control, regardless of the infection time relative to the time of BABA application.

Test 4. The effect of BABA drenched into the soil on the infection of tomato plants with *M. javanica* was examined. The experimental method was as follows.

Two ml of BABA solutions (0.2, 0.5 or 1 mg/plant) were pippeted to the soil surface around the base of the stem of tomato plants grown in 50 ml pots. Water was used as a control. One day after the treatments, plants were inoculated with 80 J2. Plants were grown in a temperature-controlled greenhouse, as described before. After 5 days, plants were uprooted, their roots were washed and stained with acid fucsin solution. Top fresh weights and the number of penetrated J2 per plant were recorded. The experiment was conducted twice with 5 replicates per treatment. Results are presented in Table 3.

TABLE 3

Effect of various doses of BABA on infection of tomato plants with *Meloidogyne javanica*

| Dose of BABA (mg/plant) | Top fresh weight (grams) | Number of J2 per plant |
|---|---|---|
| 0 | 0.46 ± 0.07 a | 44.7 ± 12.7 a |
| 0.2 | 0.37 ± 0.08 a | 34.5 ± 6.2 a |
| 0.5 | 0.36 ± 0.07 a | 13.8 ± 12.6 b |
| 1.0 | 0.32 ± 0.05 b | 6.0 ± 5.0 b |

Means within a column followed by a common letter are not different, according to Tukey's HSD (P=0.05).

Data presented in Table 3 indicate that BABA was able to protect tomato plants against nematode attack. One-half milligram per plant of BABA was sufficient to reduce by 69% the number of J2 which penetrated the roots, while 1 mg per plant reduced it by 87%.

Test 5. The effect of BABA, applied as spray, on the infection of tomato plants with *M. javanica*, was examined after infection had taken place. The experimental method was as follows.

Tomato seedlings (3-week-old) were inoculated with J2, and 5 days later the seedlings were removed from soil, roots were washed in water and then planted in uninfested soil. One day after planting, the seedlings were sprayed with 20 mM BABA Three weeks later nematode development was observed by uprooting the plants, washing their roots and staining them with acid fucsin solution. Values shown in Table 4 are means of 5 replicates. The experiment was conducted twice.

TABLE 4

Development of *Meloidogyne javanica* in tomato plants sprayed with BABA

| | 2nd-stage juveniles | 3rd-stage juveniles | 4th-stage juveniles | Small females | Large females |
|---|---|---|---|---|---|
| Control | 0.0 | 0.0 | 7.6 ± 2.5 | 15.5 ± 7.7 | 75.6 ± 5.1 |
| BABA | 4.5 ± 2.0 | 5.8 ± 1.4 | 34.7 ± 3.4 | 41.5 ± 6.1 | 13.3 ± 4.1 |

Data is presented as the percentage of nematodes in each life-stage within the overall nematode population. All data in BABA-treated plants were significantly different (P<0.05) from the corresponding data in the control (water-treated) plants.

Table 4 shows that BABA sprayed onto the foliage inhibited nematode development within the root as compared to the control (water) spray. The inhibitory effect was mostly pronounced in the large female stage, where there are six times more adult females seen after the water spray treatment (control) as compared to the BABA-treated plants.

Test 6. The effect of (R-) and (S-) enantiomers of BABA (R-BABA and S-BABA) on infection of tomato plants with *M. javanica* was examined. The experimental method was as follows.

Tomato seedlings (4-week-old) were sprayed with 2,000 ppm of BABA, R-BABA, S-BABA or water (as a control) and inoculated with 100 J2 per 50 ml pot, one day after spray. Five days after inoculation, plants were uprooted and the number of J2 per root and the galling indices were evaluated, as described befor. Values shown in Table 5 are means of 5 replicates. The experiment was conducted twice.

TABLE 5

Effect of spray with (R-) and (S-) enantiomers of β-aminobutyric acid (BABA) on infection of tomato plants with *Meloidogyne javanica*

| Treatment | J2 per root | Galling index |
|---|---|---|
| Control | 57.1 ± 12.3 a | 3.2 ± 0.4 a |
| BABA | 16.8 ± 5.7 b | 0.1 ± 0.2 c |
| S-BABA | 37.0 ± 10.5 a | 1.5 ± 0.9 b |
| R-BABA | 4.8 ± 3.3 c | 0 d |

Means within a column followed by a common letter are not different, according to Tukey's HSD (P=0 05).

Results in Table 5 show that while BABA reduced by 71% the number of J2 in the roots, R-BABA reduced it by 92% and S-BABA by only 35%. It thus appears that the activity of BABA is mainly attributed to the R-BABA enantiomer.

Test 7. The effect of repeated application of BABA on infection of tomato plants with *M. javanica* was examined. The experimental method was as follows. Tomato plants (4-week-old) were 3 times sprayed (2,000 ppm/ plant) or soil-drenched (8 ml/plant) with BABA solution at 10day-intervals. The plants were inoculated with 600 J2 per 300 ml pot, one day after the first treatment. Forty days after inoculation, the plants were harvested and the following parameters were recorded: top and root fresh weights (TFW and RFW, respectively), galling indices, and the number of eggs per root. Values presented in Table 6 are means of 5 replicates. The experiment was conducted twice.

TABLE 6

Effect of repeated treatments with BABA on infection of tomato plants with the root-knot nematode *M. javanica*

| Treatment | TFW (gr) | RFW (gr) | Galling index (scale 0–5) | No. of eggs per root (× 100) |
|---|---|---|---|---|
| Control | 5.7 ± 1.0 | 1.3 ± 0.3 | 4.6 ± 0.3 | 248.4 ± 52.0 |
| Spray 1 | 5.4 ± 1.3 | 1.1 ± 0.4 | 4.6 ± 0.2 | 81.9 ± 30.0 |
| Spray 2 | 5.8 ± 1.6 | 1.1 ± 0.4 | 4.0 ± 0.5 | 63.5 ± 24.6 |
| Spray 3 | 3.4 ± 1.0 | 0.8 ± 0.2 | 3.8 ± 0.4 | 48.0 ± 21.4 |
| Drench 1 | 6.8 ± 1.4 | 1.5 ± 0.5 | 3.0 ± 0.5 | 26.2 ± 20.8 |
| Drench 2 | 6.6 ± 1.9 | 1.4 ± 0.5 | 3.4 ± 0.6 | 34.3 ± 11.5 |
| Drench 3 | 6.6 ± 1.4 | 1.5 ± 0.4 | 3.4 ± 0.6 | 17.1 ± 8.8 |

Results presented in Table 6 show that 1, 2 and 3 sprays with BABA reduce the number of eggs by 66%, 75% and 81%, respectively, while 1, 2 and 3 soil drenches reduce it by 90%, 86% and 93%, respectively. With 40 days interval between inoculation and evaluation no significant reduction in galling was observed in BABA-sprayed plants as compared to the control.

Test 8. The effect of foliar spray with BABA in combination with the fungicide Canon® on infection of tomato plants with *M. javanica* was examined. The experimental method was as follows.

Three-week-old tomato plants were sprayed with 2,000 ppm BABA alone, 2,000 ppm Canon® (Potassium phosphite, Luxenburg Ltd Israel) alone, or a mixture (1:1, w/w) of 2,000 ppm BABA and Canon. Two days after the treatments, the plants were inoculated with about 90 J2 per 50 ml pot. Five days after inoculation plants were uprooted and the galling index and the number of J2 in roots was recorded according to the protocol described before. Values presented in Table 7 are means of 5 replicates. The experiment was conducted twice.

TABLE 7

Synergistic effect of foliar spray with BABA (BA) in combination with Canon (CA) on infection of tomato plants with the root-knot nematode *Meloidogyne javanica*

| Treatment | Concentration (ppm) | No. of J2 per root | Galling index (scale 0–5) |
|---|---|---|---|
| Control (water) |  | 50.5 ± 15.9 a | 3.7 ± 0.7 a |
| BABA | 2,000 | 21.5 ± 8.0 b | 0.56 ± 0.32 b |
| Canon ® | 2,000 | 38.1 ± 14.4 a | 0.60 ± 0.40 b |
| BA + CA (1:1) | 2,000 | 6.5 ± 6.5 c | 0.0 c |

Means within a column followed by a common letter are not different, according to Tukey's HSD (P=0.05).

The data in Table 7 show that protection with a mixture of BABA+Canon® (87%) was more effective than the added efficacies of BABA and Canon® separately (68%), as calculated according to Abbott (*J. Econ. Entomol.* 18; 265–267, 1975). The mixture of BABA and Canon® thus clearly displayed a synergistic effect.

Test 8. The efficacy of BABA against cyst nematodes in barley and wheat was examined. The experimental method was as follows.

Three-day-old barley and wheat seedlings were planted and sprayed with 2,000 ppm BABA at 10-day intervals starting one week later. On days 4, 6 and 13 after planting, the seedlings were inoculated with about 50 J2 of *Heterodera avenae*. The plants were harvested on day 97 after planting. Results are given in Table 8.

TABLE 8

The effect of sprays with BABA on infection of barley and wheat with the cyst nematode *Heterodera avenae*

| Treatment | Top F.W. | No. of cysts |
|---|---|---|
| Barley |  |  |
| Control | 6.5 ± 3.0 | 41.3 ± 5.8 |
| Spray 1 | 7.8 ± 4.0 | 47.1 ± 11.4 |
| Spray 2 | 5.0 ± 0.7 | 46.1 ± 15.3 |
| Spray 3 | 5.6 ± 0.2 | 36.3 ± 9.9 |
| Spray 4 | 4.9 ± 0.8 | 18.0 ± 5.7 |
| Spray 5 | 5.4 ± 1.9 | 10.3 ± 3.6 |
| Wheat |  |  |
| Control | 3.5 ± 0.5 | 34.5 ± 8.5 |
| Spray 1 | 3.5 ± 0.4 | 42.0 ± 8.5 |
| Spray 2 | 3.6 ± 0.2 | 33.3 ± 17.0 |
| Spray 3 | 3.2 ± 0.4 | 10.6 ± 8.0 |
| Spray 4 | 3.2 ± 0.3 | 11.8 ± 6.4 |
| Spray 5 | 3.7 ± 1.0 | 12.0 ± 4.3 |

Table 8 shows that BABA is effective in suppressing the cyst nematode *Heterodera avenae* in both barley and wheat, without affecting the fresh weight (F.W.) of the shoot. Thus, 3 sprays of BABA administered to wheat reduced the number of cysts by 66%, while the administration of 5 sprays to barley reduced the number of cysts by 75%.

Test 9. The efficacy of BABA against two cyst nematodes, *Heterodera avenae* and *Hetrodera latipons*, was examined in wheat. The experimental method was as follows.

Three-day-old wheat seedlings were planted and inoculated with about 100 J2 of *H. avenae* or *H. latipons* two days later. The seedlings were sprayed with BABA solutions on days 8 and 15 after planting. The plants were harvested 88 days after planting. Results are given in Table 9.

TABLE 9

Effect of two sprays with β-aminobutyric acid (BABA) on infection of wheat plants with the cereal cyst nematodes *Heterodera avenae* and *H. latipons*

| Treatment | Top F.W. | No. of cysts |
|---|---|---|
| *H. avenae* |  |  |
| Water | 0.9 ± 0.1 | 22.8 ± 10.0 |
| 1,000 ppm × 2 | 0.9 ± 0.1 | 23.5 ± 7.7 |
| 2,000 ppm × 2 | 1.0 ± 0.1 | 23.5 ± 6.2 |
| 3,000 ppm × 2 | 0.9 ± 0.2 | 22.8 ± 12.1 |
| 8,000 ppm × 2 | 0.8 ± 0.2 | 2.2 ± 1.1 |
| *H. latipons* |  |  |
| Water | 0.9 ± 0.1 | 12.8 ± 5.2 |
| 1,000 ppm × 2 | 0.9 ± 0.2 | 16.8 ± 10.2 |
| 2,000 ppm × 2 | 1.0 ± 0.1 | 2.7 ± 2.3 |
| 4,000 ppm × 2 | 1.0 ± 0.1 | 3.4 ± 4.5 |
| 8,000 ppm × 2 | 0.8 ± 0.2 | 0.25 ± 0.4 |

The data in table 9 show that 2 sprays of 8 mg/ml BABA suppressed cyst development of *H. avenae* by 90% and that of *H. latipons* by 98%.

Test 10. The post-infectional activity of BABA against the cereal cyst nematodes, *Heterodera avenae* and *H. latipons*, was examined in wheat. The experimental method was as follows.

Six-day-old wheat seedlings were inoculated with *H. avenae* or *H. latipons* (60 and 100 second-stage juveniles per plant, respectively), and either soil-drenched (16 ml of 2,000 ppm BABA per 100 cm3 sandy soil in a plastic pot) or sprayed twice (3-day-interval) with 8000 ppm of BABA, 3 days after inoculation. Number of nematode juveniles in roots was counted 2 weeks after inoculation. Results are given in Table 10.

TABLE 10

Post-infectional effect of BABA against two cereal cyst nematodes, *Heterodera avenae* and *H. latipons* in wheat

| Treatment | number of juveniles/plant | |
| --- | --- | --- |
|  | *H. avenae* | *H. latipons* |
| Control | 26.5 ± 5.6 | 46.1 ± 10.7 |
| 8,000 ppm × 2 sprays | 16.0 ± 2.8 | 3.5 ± 2.6 |
| 2,000 ppm soil-drench | 9.8 ± 1.7 | 7.1 ± 4.6 |

Table 10 shows that BABA reduced the number of nematodes in wheat roots even when applied 3 days after inoculation. Thus, the number of *H. latipons* juveniles was suppressed by 92% and 85%, and that of *H. avenae* juveniles by 40% and 63% as a result of the spray or soil drench, respectively.

EXAMPLE 9

Methods of Use and Compositions of the Compounds of the Present Invention

The compounds of the present invention will typically either be used as seed or tuber dressings, or will be applied to crops or their locus. If applied to crops or their locus, application will be effective either before or after infection with nematodes, and may be applied either to the foliar surfaces of the crop or by soil drenching. The amount of the active ingredient to be employed will be sufficient to induce the systemic resistance of the crop to control the nematodes and will vary depending on such factors as the species of nematode to be controlled, the method of administration (for example, spraying, drenching, dressing), the condition of the crop and the particular active ingredient used.

As a tuber or seed dressing, acceptable results may be obtained by employing from about 10 g to about 300 g of the compound of formula I per 100 kg of tuber or seed.

As an application to the crop or its locus, the compounds will be applied to the crops or to soil with a dosage rate in the range of from about 0.1 kg/ha to about 5 kg/ha, preferably from about 0,2 kg/ha to about 2 kg/ha, with application being repeated as necessary, typically at intervals of every two to four weeks.

Depending on circumstances, the compounds of this invention may be used in association with other pesticides such as fungicides, insecticides, acaricides, herbicides or plant growth regulating agents in order to enhance their activity or to widen their spectrum of activity.

The compounds of this invention are conveniently administered as compositions which include agriculturally acceptable carriers or diluents. These compositions can optionally contain, aside from a compound of formula I as the active agent, other active pesticidal agents, such as fungicides as noted above. They may be employed in either solid or liquid application forms, such as in the form of a wettable powder, an emulsion concentrate, a water dispersible suspension concentrate ("flowable"), a dusting powder, a granulate, a delayed release form, incorporating conventional carriers, diluents and/or adjuvants. Such compositions may be produced in conventional manner, e.g. by mixing the active ingredient with a carrier and other formulating ingredients.

Particular formulations to be applied as sprays, such as water dispersible concentrates or wettable powders, can optionally contain surfactants such as wetting and dispersing agents, e.g. the condensation product of formaldehyde with naphthalene sulphonate, an alkylarylsulphonate, a lignin sulphonate, a fatty alkyl sulphate, an ethoxylated alkylphenol and an ethoxylated fatty alcohol.

In general, the compositions of the present invention include from about 0.01% to about 90% by weight of active agent, the active agent consisting either of at least one compound of formula I or mixtures thereof with other active agents, such as fungicides. Concentrated forms of compositions generally contain between about 2 and about 80%, preferably between about 5 and about 70% by weight of active agent. Forms of the compositions for application may for example contain from about 0.01% to about 20% by weight, preferably from about 0.01% to about 5% by weight of active agent.

A number of examples of different formulations are given herein for illustrative purposes only and are not meant to be limiting.

Formulation Example I

Wettable Powder 50 parts by weight of compound of formula I are ground with 2 parts of lauryl sulphate, 3 parts sodium lignin sulphonate and 45 parts of finely divided kaolinite until the mean particle size is below 5 microns. The resulting wettable powder so obtained is diluted with water before use to a concentration of between about 0.01% to about 5% by weight active ingredient.

The resulting spray liquor may be applied by foliar spray as well as by root drench application.

Formulation Example II

Granulate

Onto 94.5 parts by weight of quartz sand in a tumbler mixer is sprayed 0.5 parts by weight of a binder (non-ionic tenside) and is thoroughly mixed. Five parts by weight of compound of formula I in powdered form are then added and thoroughly mixed to obtain a granulate formulation with a particle size in the range of from 0.3 to 0.7 mm. The granulate may be applied by incorporation into the soil adjacent the plants to be treated.

Formulation Example III

Emulsion Concentrate 25 parts by weight of a compound of formula I, 65 parts of xylene, 10 parts of the mixed reaction product of an alkylphenol with xyleneoxide and calcium-dodeyl-benzene sulphonate are thoroughly mixed until a homogeneous solution is obtained. The resulting emulsion concentrate is diluted with water before use.

Formulation Example IV

Seed or Tuber Dressing

Twenty-five parts by weight of a compound of formula I, 15 parts of dialkylphenoxypoly (ethylenoxy) ethanol, 15 parts of fine silica, 44 parts of fine kaolin, 0.5 parts of a colorant (e.g. crystal violet) and 0.5 parts of xanthan gum are mixed and ground in a contraplex mill at approximately 10,000 rpm to an average particle size of below 20 microns. The resulting formulation is applied to the seeds as an aqueous suspension in an apparatus suitable for that purpose. Where the compound of formula I is liquid, it is first absorbed on the carriers, if desired with the aid of a small amount of a volatile solvent such as acetone. The resulting powder is first allowed to dry if a solvent is used, then the other ingredients are added and the rest of the procedure is carried out.

What is claimed is:

1. A method for treating a crop against a disease caused by a nematode, the method comprising the step of applying a combination of a KOH-neutralized solution of $H_3PO_3$ and a compound to a portion of the crop, said compound having a formula (I):

(I)

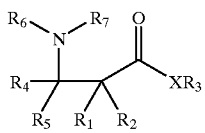

wherein $R_1$ and $R_2$ are independently selected from the group consisting of hydrogen, $C_{1-8}$ alkyl, phenyl, and phenyl-$C_{1-4}$alkyl;

$R_3$ is selected from the group consisting of hydrogen, $C_{1-23}$alkyl, carboxy-$C_{1-4}$alkyl, phenyl-$C_{1-4}$alkyl wherein the phenyl moiety is selected from the group consisting of unsubstituted and monosubstituted by halogen and $C_{2-23}$alkoxycarbonyl-$C_{1-4}$alkyl;

$R_4$ and $R_5$ are independently selected from the group consisting of hydrogen and $C_1$–$_8$alkyl;

$R_6$ and $R_7$ are independently selected from the group consisting of hydrogen, $C_1$–$_8$alkanoyl, phenyl-$C_{1-4}$ alkyl wherein the phenyl moiety is selected from the group consisting of unsubstituted and monosubstituted by halogen, $C_{2-8}$alkoxycarbonyl, $CONHR_8$ wherein $R_8$ is selected from the group consisting of hydrogen, $C_{1-8}$alkyl, phenyl, phenyl-$C_{1-4}$alkyl and phenyl-$C_{2-4}$alkyloxycarbonyl; and X is selected from the group consisting of O and S;

and salts thereof; said compound being applied in an amount sufficient to induce resistance of the crop to the nematode.

2. The method of claim 1 wherein $R_1$ and $R_2$ are independently selected from the group consisting of hydrogen, methyl and phenyl, $R_3$ is hydrogen, $R_4$ and $R_5$ are independently selected from the group consisting of hydrogen and $C_{1-3}$alkyl, $R_6$ and $R_7$ are independently selected from the group consisting of hydrogen, $C_{1-6}$alkyl and benzyl, and X is oxygen.

3. The method of claim 2 wherein $R_1$ is selected from the group consisting of hydrogen and methyl, $R_2$ is hydrogen, $R_4$ is selected from the group consisting of hydrogen and methyl, $R_5$ is hydrogen, $R_6$ is selected from the group consisting of hydrogen and methyl and $R_7$ is hydrogen.

4. The method of claim 1 wherein the compound of formula I is selected from the group consisting of R-β-aminobutyric acid and β-aminovaleric acid.

5. The method of claim 1, wherein said compound is applied by spraying onto a foliage of the crop.

6. The method of claim 1, wherein said compound is applied by drenching a root of the crop.

* * * * *